US010899705B2

(12) United States Patent
Spielmann et al.

(10) Patent No.: US 10,899,705 B2
(45) Date of Patent: Jan. 26, 2021

(54) PROCESS FOR THE MANUFACTURING OF METHANE SULFONIC ACID

(71) Applicant: BASF SE, Ludwigshafen am Rhein (DE)

(72) Inventors: Jan Spielmann, Ludwigshafen (DE); Michael Zeilinger, Ludwigshafen (DE); Juergen Wortmann, Ludwigshafen (DE); Frieder Borgmeier, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/614,599

(22) PCT Filed: May 23, 2018

(86) PCT No.: PCT/EP2018/063463
§ 371 (c)(1),
(2) Date: Nov. 18, 2019

(87) PCT Pub. No.: WO2018/219728
PCT Pub. Date: Dec. 6, 2018

(65) Prior Publication Data
US 2020/0216388 A1    Jul. 9, 2020

(30) Foreign Application Priority Data

May 30, 2017 (EP) .................................. 17173574
May 30, 2017 (EP) .................................. 17173575

(51) Int. Cl.
| | | |
|---|---|---|
| *C07C 317/04* | (2006.01) | |
| *C07C 315/06* | (2006.01) | |
| *C07C 303/06* | (2006.01) | |
| *C07C 303/44* | (2006.01) | |
| *C07C 309/04* | (2006.01) | |

(52) U.S. Cl.
CPC .......... *C07C 317/04* (2013.01); *C07C 303/06* (2013.01); *C07C 303/44* (2013.01); *C07C 309/04* (2013.01); *C07C 315/06* (2013.01)

(58) Field of Classification Search
CPC .... C07C 303/04; C07C 303/06; C07C 303/44
See application file for complete search history.

(56) References Cited

U.S. PATENT DOCUMENTS

| | | | | |
|---|---|---|---|---|
| 2,619,507 | A * | 11/1952 | Jones ........................ | C08F 4/32 568/28 |
| 4,035,242 | A * | 7/1977 | Brandt .................. | C07C 303/44 203/15 |
| 4,859,373 | A * | 8/1989 | Ollivier .................... | B01J 10/00 562/119 |
| 6,060,621 | A * | 5/2000 | Biertuempel ......... | C07C 303/02 558/39 |
| 6,960,682 | B2 * | 11/2005 | Bell ........................ | C07C 51/56 560/114 |
| 10,214,485 | B2 | 2/2019 | Spielmann et al. | |
| 10,577,312 | B2 * | 3/2020 | Spielmann .............. | B01D 3/007 |
| 2005/0070614 | A1 * | 3/2005 | Richards ................ | C07C 303/06 518/700 |
| 2006/0100458 | A1 | 5/2006 | Sen et al. | |
| 2007/0282151 | A1 * | 12/2007 | Richards ................ | C07C 303/02 585/733 |
| 2008/0161591 | A1 * | 7/2008 | Richards ................ | C07C 303/06 558/44 |
| 2016/0289176 | A1 * | 10/2016 | Ott ......................... | C07C 303/06 |
| 2016/0289181 | A1 | 10/2016 | Ott et al. | |
| 2018/0118772 | A1 * | 5/2018 | Lee ....................... | B01J 31/1815 |
| 2018/0319739 | A1 * | 11/2018 | Spielmann ........... | B01D 9/0045 |
| 2018/0327352 | A1 * | 11/2018 | Spielmann ............. | C07C 303/44 |
| 2019/0270701 | A1 * | 9/2019 | Ott ......................... | C07C 407/00 |
| 2020/0002276 | A1 * | 1/2020 | Richards ................ | C07C 407/00 |
| 2020/0039927 | A1 * | 2/2020 | Wortmann ............. | C07C 303/06 |
| 2020/0115332 | A1 * | 4/2020 | Ott ......................... | C07C 303/06 |
| 2020/0190027 | A1 * | 6/2020 | Spielmann ............. | C07C 303/44 |
| 2020/0216388 | A1 * | 7/2020 | Spielmann ............. | C07C 309/04 |

FOREIGN PATENT DOCUMENTS

| | | | | |
|---|---|---|---|---|
| CN | 101698653 A | * | 4/2010 | |
| WO | WO 2004/041399 A2 | | 5/2004 | |
| WO | WO-2004041399 A2 | * | 5/2004 | .......... C07C 303/06 |
| WO | WO 2005/069751 A2 | | 8/2005 | |

(Continued)

OTHER PUBLICATIONS

CAS Abstract Methanesulfonic Acid Anhydride (1984) (Year: 1984).*
J. Borgel et al., 140 Journal of the American Chemical Society, 16026-16031 (2018) (Year: 2018).*
CAS Abstract CN 101698653 (2010) (Year: 2010).*
L. Lobree et al., 40 Ind. Eng. Chem. Res., 736-742 (2001) (Year: 2001).*
S. Mukhopadhyay et al., Angew. Chem. Int. Ed., 1019-1021 (2003), (Year: 2003).*

(Continued)

*Primary Examiner* — Alexander R Pagano
(74) *Attorney, Agent, or Firm* — Oblon, McClelland, Maier & Neustadt, L.L.P.

(57) ABSTRACT

The present invention relates to a process for the manufacturing of methane sulfonic acid (MSA) by reaction of a radical initiator composition with methane and sulfur trioxide comprising the steps (a) preparation of the intiator composition by reacting aqueous hydrogen peroxide with the components methane sulfonic acid and methane sulfonic acid anhydride and (b) reaction of the initiator composition from step (a) with sulfur trioxide and methane to form methane sulfonic acid. The invention further relates to the use of methane sulfonic acid anhydride (MSA anhydride) in said process and to methane sulfonic acid manufactured by said process.

23 Claims, 1 Drawing Sheet

(56) References Cited

FOREIGN PATENT DOCUMENTS

| WO | WO 2007/136425 A2 | 11/2007 |
|---|---|---|
| WO | WO 2015/071365 A1 | 5/2015 |
| WO | WO 2015/071455 A1 | 5/2015 |

OTHER PUBLICATIONS

S. Mukhopadhyay et al., 211 Journal of Molecular Catalysis A: Chemical, 59-65 (2004) (Year: 2004).*
S. Mukhopadhyay et al., 347 Adv. Synth. Catal., 1203-1206 (2005) (Year: 2005).*
S. Mukhopadhyay et al., 7 Organic Process Research & Development, 754-757 (2003) (Year: 2003).*
S. Mukhopadhyay et al., Chem. Commun., 1590-1591 (2003) (Year: 2003).*
A. Shaabani et al., 49 Ind. Eng. Chem. Res., 7685-7686 (2010) (Year: 2010).*
English-Language Machine Translation CN 101698653 (2010) (Year: 2010).*
International Preliminary Report on Patentability and Written Opinion of the International Searching Authority dated Dec. 3, 2019 in PCT/EP2018/063463 filed May 23, 2018, citing document AX therein, 8 pages.
Sudip Mukhopadhyay, et al., "A High-Yield Approach to the Sulfonation of Methane to Methanesulfonic Acid Initiated by $H_2O_2$ and a Metal Chloride" Angewandte Chemie, vol. 42, Issue 26, Jul. 2, 2003, pp. 2990-2993.
Sudip Mukhopadhyay, et al., "A High-Yield, Liquid-Phase Approach for the Partial Oxidation of Methane to Methanol using $SO_3$ as the Oxidant" Advanced Synthesis & Catalysis, vol. 347, Issue 9, Jul. 19, 2005, pp. 1203-1206.
U.S. Appl. No. 15/774,847, filed May 9, 2018, US 2018/0319739 A1, Jan Spielmann, et al.
U.S. Appl. No. 16/605,973, filed Oct. 17, 2019, Juergen Wortmann, et al.
U.S. Appl. No. 16/618,283, filed Nov. 29, 2019, Jan Spielmann, et al.
International Search Report dated Jul. 25, 2018 in PCT/EP2018/063463 filed on May 23, 2018.

* cited by examiner

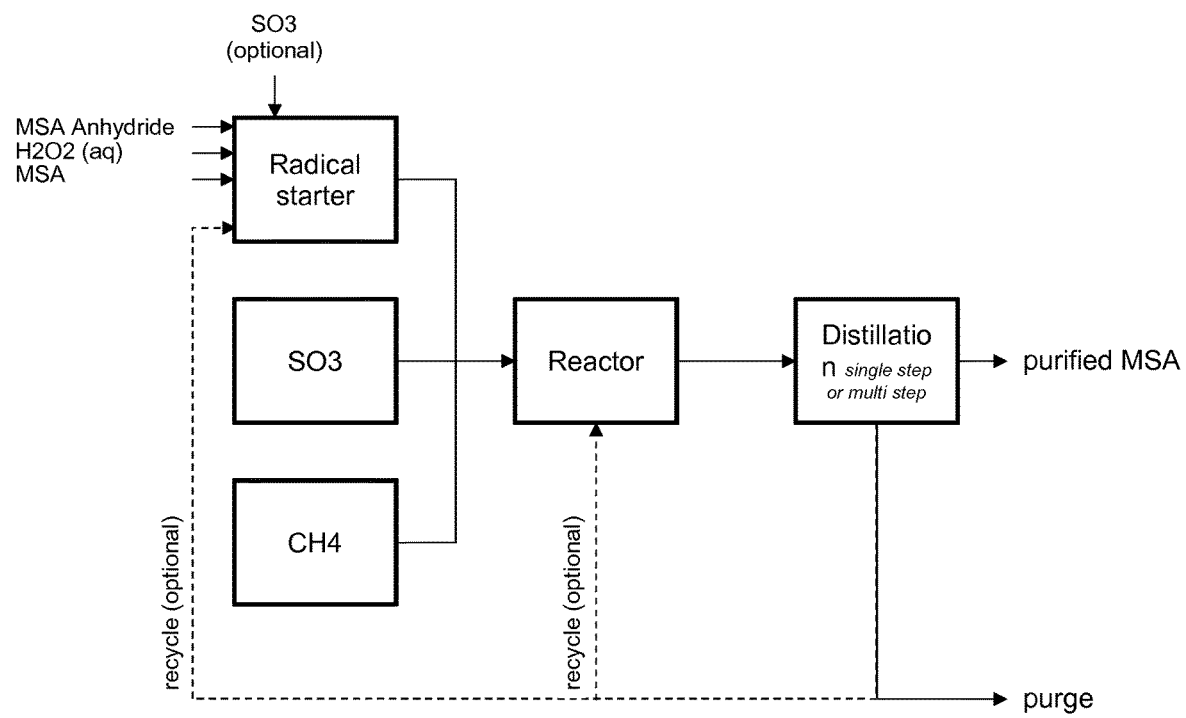

PROCESS FOR THE MANUFACTURING OF METHANE SULFONIC ACID

The present invention relates to a process for manufacturing of methane sulfonic acid (MSA), the use of methane sulfonic acid anhydride (MSA anhydride) in said process and to methane sulfonic acid manufactured by said process.

BACKGROUND OF THE INVENTION

Methane sulfonic acid (MSA) is used in different applications like for example in semiconductor industry or as rust and scale remover. As manufacturing process for MSA, different technologies are described in the art. Ideally, the manufacturing process should be cost efficient, energy saving, selective, should offer a high product yield, a low amount of byproducts and should use mild reaction conditions. Several efforts have been conducted to optimize the MSA production methods. However, for the manufacturing processes known in the art there is still a need to overcome associated disadvantages.

Mukhopadhyay et al. (Angew. Chem. Int. Ed. 2003, 42, 2990-2993) mention a synthesis of MSA via chlorine oxidation of thiomethane, which is highly productive but results in undesired couple products. As an alternative, the use of metal peroxides as radical initiator is disclosed but implies the disadvantage that metal sulfate salts are obtained as byproduct, which cannot be recycled back to the metal peroxide. Therefore, urea/$H_2O_2$ is proposed as radical initiator. However, the process is conducted in corrosive fuming sulfuric acid as solvent. As an alternative solvent, the use of MSA as solvent is disclosed in Mukhopadhyay et al. (Adv. Synth. Catal. 2005, 347, 1203-1206), however the reaction only enables 57% conversion of $SO_3$ to MSA.

US 20060100458 discloses a reaction of methane and sulfur trioxide to methane sulfonic acid by adding a solution containing $H_2S_2O_8$ to a mixture consisting of sulfur trioxide dissolved in methane sulfonic acid. $H_2S_2O_8$ acts as initiator and is prepared by passing sulfur trioxide diluted with nitrogen gas through 70% aqueous hydrogen peroxide ($H_2O_2$). Still a certain amount of sulfuric acid is obtained as byproduct which renders purification of MSA by distillation energy intensive.

WO2005069751 discloses an anhydrous processing of methane into methane sulfonic acid by a radical process using Marshall's acid or Caro's acid to create methyl radicals, which form methane sulfonic acid by combination with sulfur trioxide. As alternative initiators to form methane radicals, methane sulfonic acid anhydride is disclosed. WO2005069751 discloses to avoid the use or creation of water, which would reduce the MSA content due to formation of sulfuric acid by reaction of water with sulfur trioxide. No special attention is paid to minimize the formation of sulfuric acid. Thus a purification of MSA by distillation is energy intensive and the yield of MSA is still optimizable. In the reaction disclosed in WO2005069751 MSA is used as solvent.

WO2004041399 discloses an anhydrous processing of methane into methane sulfonic acid by a radical process to avoid the creation of waste and salts as byproducts in order to improve the selectivity and yield. The generation of water is avoided but no special attention is given to minimize the formation of sulfuric acid. Thus a purification of MSA by distillation is energy intensive and the yield of MSA is still optimizable.

WO2007136425 discloses the manufacture of dimethyl ether or olefins from methane via methane sulfonic acid, using di(methyl-sulfonyl) peroxide as radical initiator. Methane sulfonic acid anhydride is disclosed to be present when methane sulfonic acid is heated. Di(methyl-sulfonyl) peroxide is formed by electrolysis of MSA and starts a chain reaction that bonds methane to sulfur trioxide. The use of di(methyl-sulfonyl) peroxide can reduce the formation of sulfuric acid. MSA is used as solvent in order to promote greater methane solubility in the solvent. Still the amount of sulfuric acid formed in the process is not minimized and a purification of MSA by distillation is energy intensive.

WO2015071455 discloses the manufacture of MSA from methane using a mixed peroxide derived from sulfuric acid and methane sulfonic acid as radical starter or mixtures thereof as for example with sulfuric acid and/or methane sulfonic acid. The use of oleum as part of the radical initiator solution implies that unnecessary sulfuric acid is introduced into the system which makes a distillation of MSA energy consuming.

SUMMARY OF THE INVENTION

In the light of the prior art the technical problem underlying the present invention was the provision of a process for manufacturing of methane sulfonic acid (MSA) that overcomes the disadvantages of those processes known in the art. The process of the present invention is cost-efficient due to reduced energy consumption, shows increased selectivity and offers the possibility to achieve a high MSA yield. The process for manufacturing of methane sulfonic acid (MSA) enables applying of mild process conditions regarding temperature and pressure and overcomes the disadvantages known in the art.

The problem is solved by the features of the independent claims. Preferred embodiments of the present invention are provided by the dependent claims.

The invention therefore relates to a process for the manufacturing of methane sulfonic acid by reaction (preferably radical reaction) of a radical initiator composition with methane and sulfur trioxide comprising the steps:
 a) Preparation of the initiator composition by reacting aqueous hydrogen peroxide with the components methane sulfonic acid and methane sulfonic acid anhydride,
 b) Reaction of initiator composition from step a) with sulfur trioxide and methane to form methane sulfonic acid by radical reaction.

In a preferred embodiment the initiator composition in step a) further comprises sulfur trioxide.

In a preferred embodiment step a) can be divided into two sub-steps a1) and a2). In sub-step a1) methane sulfonic acid anhydride is dissolved in methanesulfonic acid and in sub-step a2) the solution from step a1) is reacted with hydrogen peroxide.

In a preferred embodiment the initiator composition in step a) or a1) further comprises a recycle stream from the bottom purge of final distillation of methane sulfonic acid comprising, preferably mainly comprising, methane sulfonic acid and sulfuric acid.

In a further preferred embodiment, the initiator composition in step a) or a1) further comprises a recycle stream from the bottom purge of final distillation of methane sulfonic acid consisting of methane sulfonic acid and sulfuric acid.

In a preferred embodiment the radical reaction in step b) comprises an initiation reaction and a propagation reaction.

In a preferred embodiment the process comprises a step c) for purification of methane sulfonic acid or methane sulfonic acid anhydride obtained from step b).

In a preferred embodiment the purification step c) is a single step distillation or a multi step distillation.

In a preferred embodiment the purification step c) for purification of MSA or MSA anhydride obtained from step b) is a crystallization followed by a solid-liquid separation.

In a preferred embodiment step a) is conducted in a reactor A, step b) is conducted in a reactor B and step c) is conducted in a column or set of columns C, and whereas reactor A, reactor B and column C are connected to conduct the process for the manufacturing of methane sulfonic acid continuously.

In a preferred embodiment step c) is conducted in a crystallization unit, where the mother liquor is recycled into the crystallization unit or into the reactor A or into the reactor B or drained.

In a preferred embodiment step c) is a combination of a distillation and a crystallization followed by solid-liquid-separation as described above.

In a preferred embodiment an additional step d), after methane sulfonic acid is obtained from step c), methane sulfonic acid anhydride is provided for subsequent charging of reactor A with methane sulfonic acid anhydride.

In a preferred embodiment the provision of methane sulfonic acid anhydride in step d) for subsequent charging of reactor A, comprises a separated methane sulfonic acid anhydride manufacturing step after step c) or a separation of methane sulfonic acid anhydride as side-component from step c).

In a preferred embodiment after step a), after the initiator composition is formed, the water content is in the range from 0 wt-% to 1 wt-%, and the content of sulfuric acid is in the range from 0 wt-% and 5 wt-% or 0 wt-% to 1 wt-%.

In a preferred embodiment after step b), after methane sulfonic acid is formed, the content of sulfuric acid is in the range from 0 wt-% to 25 wt-%, preferably 0 wt-% to 22 wt-%, more preferably 0 wt-% to 20 wt-%, even more preferably from 0 wt-% to 2 wt-%.

In a preferred embodiment after step c), after methane sulfonic acid is purified, the content of sulfuric acid is in the range from 0 ppm to 500 ppm or 0 ppm to 200 ppm.

In a preferred embodiment the temperature in step a) is in the range from −5° C. to 25° C. or −5° C. to 20° C., the temperature in step b) is in the range from 25° C. and 80° C., and the temperature in step c) in the bottom of the column is in the range from 130° C. to 240° C. If step a) is divided into two sub-steps a1) and a2), the temperature of a1) is in the range from 25° C. to 80° C. and the temperature of step a2) is in the range from −5° C. to 20° C.

In a preferred embodiment a cooling step is done between the steps a1) and a2).

In a preferred embodiment the pressure in step a) is about 1013 mbar or beyond 1013 mbar, the pressure in step b) is in the range from 10 bar to 150 bar, and the pressure in step c) at the head of the column is in the range from 1 mbar to 1000 mbar.

The invention further relates to the use of methane sulfonic acid anhydride as water scavenger for the manufacturing of methane sulfonic acid, in the step a) for the preparation of the initiator composition. According to the invention step a) can be divided into two steps a1) and a2).

In a preferred embodiment MSA anhydride is used as water scavenger, whereas methane sulfonic acid is manufactured by reaction of an initiator composition comprising aqueous hydrogen peroxide, methane sulfonic acid, optionally sulfur trioxide, optionally a recycle stream from step c) and methane sulfonic acid anhydride.

The invention further relates to the use of an initiator composition comprising methane sulfonic acid, methane sulfonic acid anhydride, optionally a recycle stream from step c) and aqueous hydrogen peroxide for the manufacturing of methane sulfonic acid.

In a preferred embodiment an initiator composition is used, whereas the initiator composition additionally comprises sulfur trioxide.

The invention further relates to MSA, whereas after purification in step c) the methane sulfonic acid content is in the range from 98 wt-% to 100 wt-% or 99 wt-% to 100 wt-%, and the sulfuric acid content is in the range from 0 ppm to 500 ppm or 0 ppm to 200 ppm.

DETAILED DESCRIPTION OF THE INVENTION

In a first aspect the invention relates to a process for manufacturing of methane sulfonic acid (MSA) by reaction of a radical initiator composition with methane and sulfur trioxide comprising the steps:
a) Preparation of the initiator composition by mixing aqueous hydrogen peroxide ($H_2O_2$) with the components methane sulfonic acid (MSA), optionally sulfur trioxide ($SO_3$) and methane sulfonic acid anhydride (MSA anhydride),
b) Reaction of the initiator composition from step a) with sulfur trioxide and methane to form MSA.

It was found that a combination of the components in step a) is suitable to form radicals as initiators for a subsequent reaction in combination with sulfur trioxide and methane. In step a) particularly the components aqueous hydrogen peroxide, methane sulfonic acid, optionally sulfur trioxide ($SO_3$), optionally a recycle stream from step c) and methane sulfonic acid anhydride are charged together in a reactor. Preferably, step a) comprises the sub-steps a1), a2) and a3). In sub-step a1) for example the components methane sulfonic acid (MSA) and methane sulfonic acid anhydride (MSA anhydride) are mixed together. In sub-step a2) aqueous hydrogen peroxide ($H_2O_2$) is added to the mixture. In step a2) for example water is removed and anhydrous conditions are for example generated, in particular due to MSA anhydride. In sub-step a3) for example sulfur trioxide ($SO_3$) is added.

In order to reduce sulfuric acid ($H_2SO_4$) content in the initiator composition in particular no oleum is added to the initiator composition, whereas in the state of the art the addition of oleum is described in for example in WO2004041399 or WO2015071455. As process conditions for preparing the initiator composition the following parameters are preferably selected in step a)
 temperature preferably in the range from −5° C. to +25° C., and
 pressure preferably in the range from 0.5 bar to 10 bar, preferably in the range from 0.8 bar to 5 bar, most preferably close to normal pressure of approximately 1 bar (about 1013 mbar).

A preferred option is to divide step a) into at least two steps a1) and a2). In that case the preferred temperature range in step a1) is between 25° C. to 80° C. while the temperature range in step a2) and potential further steps is in the range of −5° C. to 25° C. each.

The amount of MSA anhydride added to the initiator composition (starter solution) in step a) is equivalent (calculated as mol, not as gram (g)) or above equivalent to the amount of water introduced with the $H_2O_2$ solution. It is for example to note that the MSA anhydride, MSA and optionally the recycle stream from the MSA distillation are combined first, possibly at elevated temperatures, before the $H_2O_2$ solution is added to the mixture. In particular sulfur trioxide ($SO_3$) is introduced only after all free water has reacted with the MSA anhydride.

Optionally, the initiator composition in step a) further comprises sulfur trioxide ($SO_3$). A further option for the initiator composition in step a) is a recycle stream from the bottom purge of a final distillation of MSA comprising mainly MSA and $H_2SO_4$. In step a) an initiation mixture is prepared, which is suitable to form radicals at elevated temperature conditions. The formation of radicals then takes place in a so-called initiation reaction. The radicals are particularly formed in the presence of methane and/or sulfur trioxide for example as part of step b). Step a) yields a mixture comprising one or more of the components peroxomonosulfuric acid (Caro's acid), peroxo-disulfuric acid (Marshall's acid), mono(methyl-sulfonyl)peroxide (MMSP) and/or di(methyl-sulfonyl)peroxide (DMSP). These components may act as intermediates, which further form in particular methyl radicals and/or methane sulfonic acid radicals in the synthesis of MSA according to step b). Preferably, the radical reaction in step b) comprises an initiation reaction and a propagation reaction. Surprisingly, it was observed that, rather than a reaction of water in the initiator composition with sulfur trioxide ($SO_3$) to form sulfuric acid, in the present invention the amount of sulfuric acid can be minimized by adding methane sulfonic acid anhydride and still the initiator composition will promote the formation of radicals in step b).

The formation of radicals in the present invention in particular takes place in a separate step b) wherein the initiator composition from step a) is brought in contact with methane and sulfur trioxide (initiation reaction). In a subsequent reaction (propagation reaction) which is preferably also part of step b) then the formation of MSA takes place by reacting the initiator composition in a reaction with methane and sulfur trioxide. Surprisingly it was observed that the MSA obtained in this propagation reaction has a low content of sulfuric acid ($H_2SO_4$). Particularly, in presence of MSA anhydride a reduction of MSA yield caused by reaction of sulfur trioxide ($SO_3$) with water can be reduced.

Optionally, a further purification step c) may be applied in order to further purify the MSA from step b) and to further decrease the $H_2SO_4$ content in the purified MSA from step c). A purification step is for example a distillation. Surprisingly, it was observed that the energy consumption can be decreased during distillation in step c) when MSA anhydride is added in the step a) to reduce formation of sulfuric acid while forming the radicals in step b) with the initiator composition from step a).

Preferably, the process of this invention comprises a step c) for purification of MSA obtained from step b). It is further preferred that the purification step c) is a single step distillation or a multi-step distillation. Particularly during the distillation, it can be observed that the presence of MSA anhydride in step a) enables a more efficient and energy saving process for manufacturing of MSA due the to the low content of sulfuric acid in MSA after step b).

It is further preferred that the purification step c is a crystallization and/or a solid-liquid separation. Particularly during the crystallization, it can be observed that the presence of MSA anhydride in step a) enables a more efficient and energy saving process for solidification of MSA anhydride due the to the low content of sulfuric acid. The purification of MSA by crystallization can be carried out in a vessel or a set of vessels, in a heat exchanger or a set of heat exchangers, in a combination of a vessel or a set of vessels with a heat exchanger or a set of heat exchangers.

It is another option that the purification step c is a combination of a distillation, realized as single step distillation or a multi-step distillation, with a crystallization and/or a solid-liquid separation.

It is preferred that step a) is conducted in a reactor A, step b) is conducted in a reactor B and step c) is conducted in a column or in a set of columns C, and whereas the reactor A, reactor B and column C are connected to conduct the process for the manufacturing of MSA continuously. If step c) is carried out in a multi-step distillation the first purification step can be carried out in a simple vessel which can be stripped with a carrier gas or operated under vacuum as indicated below. Stripping by addition of a gaseous carrier is being regarded as a distillative or evaporative process.

Preferably, in an additional step d), after MSA is obtained from step b) or c) respectively, MSA anhydride is provided for subsequent charging of reactor A with MSA anhydride.

Preferably, step d) for providing MSA anhydride for subsequent charging of reactor A comprises a separated MSA anhydride manufacturing step after step c) or MSA anhydride is provided for subsequent charging of reactor A by separation of MSA anhydride as side-product from step c).

Preferably, prior to starting the synthesis/reaction sequence, the equipment used for steps a) to d) is set under inert conditions, e.g. by rinsing with inert gases as nitrogen or argon, by repeated evacuation of the system and refilling the system with inter gases or by other means yielding the same effect. In particular, step a) and b) should be carried out under inert conditions.

Preferably, the molar ratio of MSA anhydride to water in step a) is in the range from 1.0 mol MSAA:1.0 mol H2O to 1.0:5.0 mol/mol, more preferably in the range from 1.0:1.0 mol/mol to 1.0:2.5 mol/mol and most preferably in the range from 1.0:1.0 mol/mol to 1.0:1.5 mol/mol or any value between these values or ranges thereof.

Preferably, after step a), after the initiator composition is formed, the water content is preferably in the range from 0 wt-% to 1 wt-%, more preferably in the range from 0 wt-% to 0.1 wt-% and most preferably about 0 wt-%. The content of sulfuric acid after step a), after the initiator composition is formed, is preferably in the range from 0 wt-% to 5.0 wt-%, preferred it is in the range from 0 wt-% and 2.0 wt-%, most preferred in the range from 0 wt-% to 1.0 wt-%. It is in particular preferred that the content of sulfuric acid after step a), after the initiator composition is formed, is about 0.2 wt-%, 0.4 wt-%, 0.6 wt-%, 0.8 wt-% or any value between these values or ranges thereof.

Preferably, after step b), after methane sulfonic acid is formed, the content of sulfuric acid after step b), after methane sulfonic acid is formed, is preferably in the range from 0 wt-% to 20 wt-%, preferred in the range from 0 wt-% to 15 wt-% and most preferred from 0 wt-% to 10 wt-% or even from 0 wt-% to 8 wt-%. It is in particular preferred that the content of sulfuric acid after step b), after methane sulfonic acid is formed, is about 1 wt-%, 2 wt-%, 3 wt-%, 4 wt-%, 5 wt-%, 6 wt-%, 7 wt-%, or any value between these values or ranges thereof.

Preferably, for example after step c), after MSA is purified, the content of sulfuric acid after step c), after MSA is purified, is preferably in the range from 0 ppm to 500 ppm, preferred in the range from 0 ppm to 300 ppm or 0 ppm to 200 ppm, and most preferred in the range from 0 ppm to 100 ppm. It is in particular preferred that the content of sulfuric acid after step c), after MSA is purified, is for example 80 ppm or lower, is for example 60 ppm or lower, is for example 50 ppm or lower, or any value between these values or ranges thereof.

Preferably, the temperature in step a) is in the range from −5° C. to +25° C. or −5° C. to 20° C., more preferably in the range from −2° C. to +20° C. and most preferably in the range from 0° C. to 15° C., or any value between these values or ranges thereof. If step a) is divided into at least two sub-steps a1) and a2) the temperature in sub-step a1) is in the range from 25° C. to 80° C., preferred from 30° C. to 70° C. while the temperature in sub-step a2) and potential further steps is in the range from −5° C. to +25° C., more preferably in the range from −2° C. to +20° C. and most preferably in the range from 0° C. to 15° C., or any value between these values or ranges thereof. Preferably, the temperature in step b) is in the range from 25° C. to 80° C., more preferably in the range from 30° C. to 70° C. and most preferably in the range from 40° C. to 60° C., or any value between these values or ranges thereof. Preferably, the temperature at the bottom of the column in step c) is in the range from 130° C. to 240° C., more preferably in the range from 150° C. to 200° C., or any value between these values or ranges thereof. If the distillation in step c) is carried out in two or more steps, the first step can be operated for example at temperatures in the range from 100° C. to 200° C., preferably in the range from 130° C. to 195° C., and more preferably in the range from 150° C. to 190° C., or any value between these values or ranges thereof.

Preferably, the pressure in step a) can be any pressure, preferably a pressure close to normal conditions or for example slightly increased pressures, in particular in the range from 0.5 bar to 10 bar, more preferably in the range from 0.8 bar to 5 bar and most preferably at about 1013 mbar or for example at slightly elevated pressure beyond 1013 mbar e.g. 2 bar (absolute), or any value between these values or ranges thereof. The same holds for each step if step a) is divided into two or more sub-steps a1), a2) etc. The pressure in step b) is preferably in the range from 10 bar to 150 bar, more preferably in the range from 20 bar to 100 bar, and most preferably in the range from 40 bar to 80 bar, or any value between these values or ranges thereof. The pressure in step c) is preferably in the range from 2 mbar to 1000 mbar, preferred in the range from 2 mbar to 300 mbar and most preferred in the range from 5 to 100 mbar, or any value between these values or ranges thereof. If the distillation in step c) is carried out in two or more steps, the first step can be operated at pressures in the range from 5 mbar to 1000 mbar, preferably in the range from 7 mbar to 500 mbar, and most preferably in the range from 10 mbar to 200 mbar, or any value between these values or ranges thereof. The second step can be carried out at a pressure between 1 and 30 mbar, preferably between 2 and 20 mbar and most preferred between 5 and 15 mbar.

A further aspect of the invention relates to the use of MSA anhydride as water scavenger for the manufacturing of MSA, especially in the synthesis step a) for the preparation of the initiator composition. In particular the initiator composition is suitable to act as radical starter.

Preferably, MSA anhydride is used as water scavenger, whereas MSA is manufactured by reaction of methane and SO3 with an initiator composition comprising aqueous $H_2O_2$, MSA, optionally $SO_3$, optionally sulfuric acid and MSA anhydride. Instead of sulfur trioxide ($SO_3$) the initiator composition can be fed with a recycle stream from the bottom purge of the final distillation of MSA comprising mainly MSA and $H_2SO_4$.

A further aspect of the invention relates to the use of an initiator composition comprising MSA, optionally $SO_3$ or a recycle stream from the bottom purge of the final distillation of MSA comprising mainly MSA and $H_2SO_4$, MSA anhydride and aqueous $H_2O_2$ for the manufacturing of MSA.

A further aspect of the invention relates to methanesulfonic acid (MSA), whereas after purification in step c) the MSA content is preferably in the range from 98 wt-% to 100 wt-%, preferred in the range from 99 wt-% to 100 wt-% and most preferred in the range from 99.5 wt-% to 100 wt-%, or any value between these values or ranges thereof. It is in particular preferred that after purification in step c) the MSA content is about 99.1 wt-%, 99.2 wt-%, 99.3 wt-%, 99.4 wt-%, 99.6 wt-%, 99.7 wt-%, 99.8 wt-%, 99.9 wt-%. It is further preferred that after purification in step c) the $H_2SO_4$ content is preferably in the range from 0 ppm to 500 ppm, preferred in the range from 0 ppm to 300 ppm or 0 ppm to 200 ppm, and most preferred in the range from 0 ppm to 100 ppm or even from 0 ppm to 50 ppm or lower, or any value between these values or ranges thereof. It is in particular preferred that after purification in step c) the sulfuric acid content is in the range from 0 ppm to 40 ppm, preferably in the range form 0 ppm to 30 ppm, more preferably in the range from 0 ppm to 20 ppm and most preferably in the range from 0 ppm to 10 ppm, or any value between these values or ranges thereof.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods know to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferable within 10%, and more preferably within 5% of a given value or range. The term "about" or "approximately" as used herein also includes the exact respective values or ranges.

Throughout the specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude material or steps that do not materially affect the basic and novel characteristics of the claim.

Summarizing, the present invention describes an easy way to reduce the content of sulfuric acid in MSA synthesis by adding MSA anhydride as water scavenger to the synthesis of the radical starter. By offering MSA anhydride the formation of additional sulfuric acid through reaction of H2O (unavoidably introduced with H2O2 as H2O2 is always provided as aqueous solution) with SO3 is avoided while at the same time MSA anhydride is hydrolyzed to the target molecule MSA. Moreover, the reduction of sulfuric acid content in the mixture reduces the energy demand required for purification of MSA. And finally, a low sulfuric acid concentration helps to increase the MSA yield.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

FIGURES

The invention is further described by the following FIGURE. The FIGURE relates to schematic and in some cases preferred embodiment of the invention that do not limit the scope of the invention.

FIG. 1 is for example a schematic exemplified diagram of the process of the present invention.

EXAMPLES

1) MSA Anhydride as Water Scavenger
2 g MSA anhydride (purchased from Aldrich, purified by sublimation) was dissolved in 50 g MSA (99.99 wt-%) at room temperature under stirring. Under continuous stirring 1.02 equivalents of water—relative to MSAA—were added to the mixture at room temperature.
Hydrolysis of MSAA to MSA was followed by $^1$H NMR (Bruker Avance III HD 400 MHz, $C_6D_6$ was used in a capillary as the lock reference. The following NMR-shifts were used to identify and quantify the respective compounds:

| Substance | $^1$H-NMR shift [ppm] |
|---|---|
| MSA ($H_3C$—$SO_3H$) | $\delta(^1H, CH_3) = 3.43$ |
| MSA Anhydride ($H_3C$—$SO_2$—O—$SO_2$—$CH_3$) | $\delta(^1H, CH_3) = 3.7$ |

After ca. 5 h 50% of the MSA anhydride hydrolyzed to MSA and after 5 d 75% of the MSA anhydride hydrolyzed to MSA.
To finalize hydrolyzation the mixture was heated to 50° C., a sample was taken after 3 h and immediately analyzed by $^1$H NMR. No MSAA could be found in this sample any more.

2) MSA Anhydride as Water Scavenger in the Presence of Hydrogen Peroxide
1.25 g MSA anhydride (purchased from Aldrich, purified by sublimation) were dissolved in 50 g MSA (99.99 wt-%) at room temperature under stirring. To this solution 0.46 g of a H2O2 solution (70 wt-%) were added by syringe at room temperature. The corresponding peroxide content at the beginning of the experiment was 0.6 wt-%.
Hydrolysis of MSAA to MSA was followed by $^1$H NMR as described above.
After ca. 3 d and ca. 7 d (control sample) samples were taken and analyzed by $^1$H NMR. Neither in the 3 d nor in the 7 d sample MSAA could be found any more. The peroxide content slightly dropped to 0.4 wt-% after 7 d.

Energy Savings in MSA Distillation

To show the beneficial effect of a reduced concentration of sulfuric acid in the synthesis creating a raw MSA for purification, e.g. achieved according to this invention by using MSA anhydride as water scavenger in the synthesis of the radical starter solution, two process simulations were carried out, the first with a sulfuric acid concentration of 20 wt-% and the second with a reduced amount of 18 wt-%.

In the following examples reference compositions for the feed to the distillation ("raw MSA") were chosen which cover a range of raw MSA compositions to be expected according to own experiments and to literature. To develop a distillation concept this raw MSA needs to comprise at least one compound representing the low boilers, at least one compound representing the high boilers and of course the target product MSA. For the process simulations in the following examples MSAA and methylmethanesulfonate (MMS) were selected as low boilers and sulfuric acid was selected as high boiler. The amount of sulfuric is varied to demonstrate the potential to save energy when reducing sulfuric acid concentration in the feed to the distillation.

In the process simulation the content of sulfuric acid in the purified MSA was pre-defined (e.g. 10 ppm), other parameters as distillation yield, MSA content of the purified MSA, mass flow and composition of the purge streams, and temperatures at the bottom of the distillation columns were a result of the simulation. As these parameters are not completely independent of one another the following examples target just to show the principle effect of certain parameters in the inventive purification step. A person skilled in the art will be aware that e.g. the yield of the distillation process could be increased, but at the cost of e.g. a higher energy consumption. In the same sense the purity of MSA could be increased, but at the cost of e.g. an increased high boiler purge stream and thus of lower purification yields.

The formation of MMS or other side products by thermal decomposition of MSA (and/or potential consecutive reactions of the decomposition products) was not integrated in the process simulation in the form of a temperature-dependent reaction. This would have added a huge amount of complexity to the simulation, a complexity which is not needed to show the effect of the current invention.

In the following examples MSA yields are given as wt-% and calculated as follows:

$$\frac{MSA \text{ in feed [kg/h]} - MSA \text{ in purge [kg/h]}}{MSA \text{ in feed [kg/h]}}$$

Example 3 (Feed to Distillation with 20 wt-% Sulfuric Acid)

Raw MSA from the reaction of methane and SO3 was purified in a two-column set-up as described in the BASF unpublished patent application no. EP 17173574.9. The raw MSA consisted of 78.8 wt-% MSA, 20.0 wt-% sulfuric acid, 0.2 wt-% MSA anhydride, 0.1 wt-% methane and ca. 160 ppm methylmethanesulfonate. The MSA mass flow was 2000 kg/h. The raw MSA was sent to the distillation after depressurizing the mixture from a pressure in the synthesis unit of ca. 100 bar to 1 bar in a flash unit.

In a first distillation step (column 1), light boilers are removed from raw MSA at the top of the column (ca. 30 kg/h) and purified MSA is removed via side discharge ($T_{MSA}$ at discharge 163° C.). In the second distillation step (column 2) MSA is depleted of high boilers, especially of sulfuric acid. One fraction of the high boilers is purged from the second column via a discharge line at the bottom (purge: 643 kg/h, 21 wt-% MSA, 79 wt-% sulfuric acid), the rest is returned to column 1.

Column 1 is operated at a pressure of 10 mbar at the head of the column and 20 mbar at the bottom of the column (gas phase above sump), the temperature at the bottom of the column is 198° C. The column has a diameter of 1700 mm, the f-factor is 1.9 $Pa^{0.5}$ (theoretical number of trays 12, plus partial condenser). Column 2 is operated with a pressure of 10 mbar at the head of the column (practically no pressure drop as no column internals), the temperature at the bottom of the column is 188° C. The column has a diameter of 2400 mm, the f-factor is 0.45 $Pa^{0.5}$ (theoretical number of trays 2, plus total condenser). The energy required to evaporate the raw MSA in column 1 was provided by a heat exchanger ("Zwangsumlaufverdampfer") connected to the bottom of column 1 and circulated by a pump. The same applies for the set-up of column 2.

MSA was obtained with a yield of 93.2%, the resulting MSA had a purity of 99.7 wt-%. The impurities in the purified MSA stream are as follows. The content of sulfuric acid is 10 ppm. The content of methylmethanesulfonate is 7 ppm. The content of MSA anhydride is ca. 0.3 wt-%. The energy consumption for the evaporation is 881 kWh (evaporation energy only, no condensation energy, no pumping energy).

Example 4 (Feed to Distillation with 18 wt-% Sulfuric Acid)

The same process simulation and the same distillation conditions (e. g. pressures, temperatures) were used as in example 3. The only difference was that the concentration of sulfuric acid in the feed to the distillation was reduced from 20 wt-% to 18 wt-% assuming that the formation of an incremental amount of sulfuric acid could be suppressed by applying MSA anhydride as water scavenger in the synthesis of the radical starter according to this invention. The reduced amount of sulfuric acid was replaced by additional MSA in the feed stream. The total amount of MSA was kept constant at 2000 kg/h.

The lower sulfuric acid concentration in the feed to the distillation allows to reduce the purge from 643 kg/h to 557 kg/h, at the same time the MSA yield increases from 93.2% to 94.5% and the energy consumption for the evaporation drops from 881 kWh to 775 kWh (evaporation energy only, no condensation energy, no pumping energy).

The invention claimed is:

1. A process of manufacturing methane sulfonic acid by reacting a radical initiator composition with methane and sulfur trioxide, the process comprising:
   a) preparing the radical initiator composition by reacting aqueous hydrogen peroxide with methane sulfonic acid and methane sulfonic acid anhydride, and
   b) reacting the radical initiator composition of a) with sulfur trioxide and methane to form methane sulfonic acid.

2. The process of claim 1, wherein the radical initiator composition of a) further comprises sulfur trioxide.

3. The process of claim 1, wherein the radical initiator composition of a) further comprises a recycle stream from a bottom purge of a final distillation of methane sulfonic acid, comprising methane sulfonic acid and sulfuric acid.

4. The process of claim 1, wherein b) comprises an initiation reaction and a propagation reaction.

5. The process of claim 1, further comprising c) purifying the methane sulfonic acid formed in b).

6. The process of claim 1, further comprising c) purifying the methane sulfonic acid form in b) by a single step distillation.

7. The process of claim 1, further comprising c) purifying the methane sulfonic acid foamed in b) by a crystallization followed by a solid-liquid separation.

8. The process of claim 1, wherein
   a) is conducted in a reactor A, and
   b) is conducted in a reactor B, and the process further comprises
   c) purifying the methane sulfonic acid formed in b) in a column or set of columns C,
   wherein the reactor A, the reactor B and the column or set of columns C are connected to conduct the process continuously.

9. The process of claim 1, wherein
   a) is conducted in a reactor A, and
   b) is conducted in a reactor B, and the process further comprises
   c) purifying the methane sulfonic acid formed in b in a crystallization unit, where a mother liquor is recycled into the crystallization unit or into the reactor A or into the reactor B or drained.

10. The process of claim 1, wherein a) is conducted in a reactor A, and the process further comprises:
    c) purifying the methane sulfonic acid formed in b), to obtain a purified methane sulfonic acid, and then
    d) providing methane sulfonic acid anhydride for subsequently charging the reactor A with methane sulfonic acid anhydride.

11. The process of claim 1, wherein a) is conducted in a reactor A, and the process further comprises:
    c) purifying the methane sulfonic acid formed in b), to obtain a purified methane sulfonic acid, and then
    d) providing methane sulfonic acid anhydride for subsequently charging the reactor A with methane sulfonic acid anhydride,
    wherein d) comprises separately manufacturing methane sulfonic acid anhydride or separating methane sulfonic acid anhydride as a side-component from c).

12. The process of claim 1, wherein after a), after the radical initiator composition is formed, a water content is in a range of from 0 wt-% to 1 wt-% and a content of sulfuric acid is in a range of from 0 wt-% to 5 wt-%.

13. The process of claim 1, wherein after b), after methane sulfonic acid is formed, a content of sulfuric acid is in a range of from 0 wt-% to 25 wt-%.

14. The process of claim 1, further comprising c) purifying the methane sulfonic acid formed in b),
    wherein after c), after methane sulfonic acid is purified, a content of sulfuric acid is in a range of from 0 ppm to 500 ppm.

15. The process of claim 1, further comprising c) purifying the methane sulfonic acid formed in b),
    wherein a temperature in a) is in a range of from −5° C. to 25° C.,
    a temperature in b) is in a range of from 25° C. and 80° C., and a temperature in c) in a bottom of a column is in a range of from 130° C. to 240° C.

16. The process of claim 1, wherein a) comprises two sub-steps a1) and a2),
wherein a temperature in sub-step a1) is in a range of from 25° C. to 80° C. and
a temperature range in sub-step a) and in optional further sub-steps is in a range of −5° C. to 25° C. each.

17. The process of claim 1, wherein a pressure in a) is about 1013 mbar or beyond 1013 mbar,
a pressure in b) is in a range of from 10 bar to 150 bar, and
a pressure in c) in a bottom of a column is in a range of from 2 mbar to 1000 mbar.

18. A method of manufacturing methane sulfonic acid, the method comprising
a) preparing an initiator composition,
wherein a) comprises scavenging water with methane sulfonic acid anhydride,
wherein the methane sulfonic acid is manufactured by a radical reaction, and the initiator composition comprises aqueous hydrogen peroxide, methane sulfonic acid, optionally sulfur trioxide, optionally sulfuric acid and methane sulfonic acid anhydride.

19. A method of manufacturing methane sulfonic acid, the method comprising preparing the methane sulfonic acid by a radical reaction comprising an initiator composition comprising methane sulfonic acid, methane sulfonic acid anhydride and aqueous hydrogen peroxide.

20. The method of claim 19, wherein the initiator composition further comprises sulfur trioxide.

21. The method of claim 19, wherein the initiator composition further comprises sulfuric acid.

22. The process of claim 1, further comprising c) purifying the methane sulfonic acid form in b) by a multi step distillation.

23. The process of claim 1, further comprising c) purifying the methane sulfonic acid formed in b),
wherein after c), after methane sulfonic acid is purified, a content of sulfuric acid is in a range of from 0 ppm to 200 ppm.

* * * * *